US 9,937,358 B2

(12) United States Patent
Schwarz et al.

(10) Patent No.: US 9,937,358 B2
(45) Date of Patent: Apr. 10, 2018

(54) AESTHETIC METHODS OF BIOLOGICAL STRUCTURE TREATMENT BY MAGNETIC FIELD

(71) Applicant: BTL HOLDINGS LIMITED, Nicosia (CY)

(72) Inventors: Tomáš Schwarz, Prague (CZ); Ondra Prouza, Říčany u Prahy (CZ)

(73) Assignee: BTL Holdings Limited, Nicosia (CY)

( * ) Notice: Subject to any disclaimer, the term of this patent is extended or adjusted under 35 U.S.C. 154(b) by 0 days.

(21) Appl. No.: 15/446,951

(22) Filed: Mar. 1, 2017

(65) Prior Publication Data
US 2017/0173347 A1 Jun. 22, 2017

Related U.S. Application Data

(63) Continuation-in-part of application No. 15/396,073, filed on Dec. 30, 2016, which is a continuation-in-part of application No. 15/178,455, filed on Jun. 9, 2016, which is a continuation-in-part of application No. 15/151,012, filed on May 10, 2016, which is a continuation-in-part of application No. 15/099,274, filed on Apr. 14, 2016, which is a continuation-in-part of application No. 15/073,318, filed on Mar. 17, 2016, which is a continuation-in-part of application No. 14/951,093, filed on Nov. 24, 2015, which is a continuation-in-part of application No. 14/926,365, filed on Oct. 29, 2015, now abandoned, which is a continuation-in-part of application No. 14/789,658,
(Continued)

(51) Int. Cl.
*A61N 2/00* (2006.01)
*A61N 2/02* (2006.01)

(52) U.S. Cl.
CPC ............ *A61N 2/006* (2013.01); *A61N 2/004* (2013.01); *A61N 2/02* (2013.01)

(58) Field of Classification Search
CPC .......... A61N 2/00; A61N 2/002; A61N 2/004; A61N 2/006; A61N 2/008; A61N 5/06; A61K 41/0004
USPC ......................................................... 600/9–15
See application file for complete search history.

(56) References Cited

U.S. PATENT DOCUMENTS 3,163,161 A 12/1964 Courtin
3,915,151 A 10/1975 Kraus
(Continued)

FOREIGN PATENT DOCUMENTS

EP 0209246 A1 1/1987
EP 2676700 A2 12/2013
(Continued)

OTHER PUBLICATIONS

The Burn Centre Care, Education, 3 pages, printed from internet Nov. 13, 2017.*
(Continued)

*Primary Examiner* — Samuel Gilbert
(74) *Attorney, Agent, or Firm* — Kenneth H. Ohriner; Perkins Coie LLP (57) ABSTRACT

In a method for stimulation and treatment of a biological structure of a patient, the biological structure is treated by high power time-varying magnetic field. The treatment is followed by at least a partial muscle contraction. The method may be used in applications for non-invasive aesthetic medicine.

11 Claims, 4 Drawing Sheets

Related U.S. Application Data filed on Jul. 1, 2015, which is a continuation-in-part of application No. 14/789,156, filed on Jul. 1, 2015.

(56) References Cited

U.S. PATENT DOCUMENTS

| | | | |
|---|---|---|---|
| 4,237,898 A | 12/1980 | Whalley | |
| 4,665,898 A | 5/1987 | Costa et al. | |
| 4,674,505 A | 6/1987 | Pauli et al. | |
| 4,993,413 A | 2/1991 | McLeod et al. | |
| 5,085,626 A | 2/1992 | Frey | |
| 5,143,063 A | 9/1992 | Fellner | |
| 5,401,233 A | 3/1995 | Erickson et al. | |
| 5,433,740 A | 7/1995 | Yamaguchi | |
| 5,766,124 A | 6/1998 | Polson | |
| 5,807,232 A | 9/1998 | Espinoze et al. | |
| 5,984,854 A | 11/1999 | Ishikawa et al. | |
| 6,047,215 A | 4/2000 | McClure et al. | |
| 6,063,108 A | 5/2000 | Salansky et al. | |
| 6,117,066 A | 9/2000 | Abrams | |
| 6,179,769 B1 | 1/2001 | Ishikawa et al. | |
| 6,213,933 B1 | 4/2001 | Lin | |
| 6,223,750 B1 | 5/2001 | Ishikawa et al. | |
| 6,261,301 B1 | 7/2001 | Knesch et al. | |
| 6,334,074 B1 | 12/2001 | Spertell | |
| 6,350,276 B1* | 2/2002 | Knowlton | A45D 44/22 607/101 |
| 6,402,678 B1 | 6/2002 | Fischell et al. | |
| 6,413,255 B1 | 7/2002 | Stern | |
| 6,418,345 B1 | 7/2002 | Tepper et al. | |
| 6,527,694 B1 | 3/2003 | Ishikawa et al. | |
| 6,569,078 B2 | 5/2003 | Ishikawa et al. | |
| 6,605,080 B1 | 8/2003 | Altshuler et al. | |
| 6,939,287 B1 | 9/2005 | Ardizzone et al. | |
| 7,030,764 B2 | 4/2006 | Smith et al. | |
| 7,601,115 B2 | 10/2009 | Riehl | |
| 7,630,774 B2 | 12/2009 | Karni et al. | |
| 7,643,883 B2 | 1/2010 | Kreindel | |
| 7,740,574 B2 | 6/2010 | Pilla et al. | |
| 7,744,523 B2 | 6/2010 | Epstein | |
| 7,946,973 B2 | 5/2011 | Peterchev | |
| 7,998,053 B2 | 8/2011 | Aho | |
| 8,088,058 B2 | 1/2012 | Juliana et al. | |
| 8,548,599 B2 | 10/2013 | Zarsky et al. | |
| 9,002,477 B2 | 4/2015 | Burnett | |
| 9,586,057 B2 | 3/2017 | Ladman et al. | |
| 2001/0031906 A1 | 10/2001 | Ishikawa et al. | |
| 2002/0010414 A1 | 1/2002 | Coston et al. | |
| 2004/0015163 A1 | 1/2004 | Buysse et al. | |
| 2004/0073079 A1 | 4/2004 | Altshuler et al. | |
| 2005/0049543 A1 | 3/2005 | Anderson et al. | |
| 2005/0203504 A1 | 9/2005 | Wham et al. | |
| 2006/0152301 A1 | 7/2006 | Rohwedder | |
| 2006/0187607 A1 | 8/2006 | Mo | |
| 2006/0195168 A1 | 8/2006 | Dunbar et al. | |
| 2006/0206180 A1 | 9/2006 | Alcidi | |
| 2007/0135811 A1 | 6/2007 | Hooven | |
| 2007/0173805 A1 | 7/2007 | Weinberg et al. | |
| 2007/0244530 A1 | 10/2007 | Ren | |
| 2007/0270795 A1 | 11/2007 | Francischelli et al. | |
| 2008/0009885 A1 | 1/2008 | Del Giglio | |
| 2008/0082094 A1 | 4/2008 | McPherson et al. | |
| 2008/0183251 A1 | 7/2008 | Azar et al. | |
| 2008/0228520 A1 | 9/2008 | Day et al. | |
| 2008/0249350 A1 | 10/2008 | Marchitto et al. | |
| 2008/0255572 A1 | 10/2008 | Zeller et al. | |
| 2008/0262287 A1 | 10/2008 | Dussau | |
| 2008/0287948 A1 | 11/2008 | Newton et al. | |
| 2008/0312647 A1 | 12/2008 | Knopp et al. | |
| 2009/0005631 A1 | 1/2009 | Simenhaus et al. | |
| 2009/0018628 A1 | 1/2009 | Burns et al. | |
| 2009/0221938 A1 | 9/2009 | Rosenberg et al. | |
| 2009/0248004 A1 | 10/2009 | Altshuler et al. | |
| 2009/0306648 A1 | 12/2009 | Podhajsky et al. | |
| 2010/0087699 A1 | 4/2010 | Peterchev | |
| 2010/0087816 A1 | 4/2010 | Roy | |
| 2010/0121131 A1 | 5/2010 | Mathes | |
| 2010/0179372 A1 | 7/2010 | Glassman | |
| 2010/0228250 A1 | 9/2010 | Brogna | |
| 2010/0286691 A1 | 11/2010 | Kerr et al. | |
| 2010/0331603 A1 | 12/2010 | Szecsi et al. | |
| 2011/0021863 A1 | 1/2011 | Burnett et al. | |
| 2011/0046523 A1 | 2/2011 | Altshuler et al. | |
| 2011/0202058 A1 | 8/2011 | Eder et al. | |
| 2011/0245900 A1 | 10/2011 | Turner et al. | |
| 2011/0263925 A1 | 10/2011 | Bratton | |
| 2012/0016359 A1 | 1/2012 | Podhajsky | |
| 2012/0029394 A1 | 2/2012 | Babaev | |
| 2012/0046598 A1 | 2/2012 | Kardos et al. | |
| 2012/0053449 A1 | 3/2012 | Moses et al. | |
| 2012/0150079 A1 | 6/2012 | Rosenberg | |
| 2012/0226272 A1 | 9/2012 | Chernov et al. | |
| 2013/0030239 A1 | 1/2013 | Weyh et al. | |
| 2013/0123568 A1 | 5/2013 | Hamilton et al. | |
| 2013/0123765 A1 | 5/2013 | Zarsky et al. | |
| 2013/0144280 A1 | 6/2013 | Eckhouse et al. | |
| 2013/0150653 A1 | 6/2013 | Borsody | |
| 2013/0158634 A1 | 6/2013 | Ron Edoute et al. | |
| 2013/0178764 A1 | 7/2013 | Eckhouse et al. | |
| 2013/0238061 A1 | 9/2013 | Ron Edoute et al. | |
| 2013/0261683 A1 | 10/2013 | Soikum et al. | |
| 2013/0303904 A1 | 11/2013 | Barthe et al. | |
| 2013/0317281 A1 | 11/2013 | Schneider et al. | |
| 2014/0046423 A1 | 2/2014 | Rajguru et al. | |
| 2014/0249609 A1 | 9/2014 | Zarsky et al. | |
| 2014/0257071 A1 | 9/2014 | Curran et al. | |
| 2014/0303525 A1 | 10/2014 | Sitharaman | |
| 2014/0350438 A1 | 11/2014 | Papirov et al. | |
| 2015/0025299 A1 | 1/2015 | Ron Edoute et al. | |
| 2015/0123661 A1 | 5/2015 | Yui et al. | |
| 2015/0133717 A1 | 5/2015 | Ghiron et al. | |
| 2015/0141877 A1 | 5/2015 | Feldman | |
| 2015/0157873 A1 | 6/2015 | Sokolowski | |
| 2015/0165238 A1 | 6/2015 | Slayton et al. | |
| 2015/0216719 A1 | 8/2015 | Debenedictis et al. | |
| 2015/0238248 A1 | 8/2015 | Thompson et al. | |
| 2015/0238771 A1 | 8/2015 | Zarsky et al. | |
| 2015/0328475 A1 | 11/2015 | Kim et al. | |
| 2015/0367141 A1 | 12/2015 | Goetz et al. | |
| 2016/0016013 A1 | 1/2016 | Capelli et al. | |
| 2016/0030763 A1 | 2/2016 | Midorikawa et al. | |
| 2016/0051827 A1 | 2/2016 | Ron Edoute et al. | |
| 2016/0066977 A1 | 3/2016 | Neal, II et al. | |
| 2016/0250494 A1 | 9/2016 | Sakaki et al. | |

FOREIGN PATENT DOCUMENTS

| | | | |
|---|---|---|---|
| WO | 2002025675 A1 | 3/2002 | |
| WO | 2003090863 A1 | 11/2003 | |
| WO | 2004087255 A1 | 10/2004 | |
| WO | 2008109058 A1 | 9/2008 | |
| WO | 2010007614 A3 | 1/2010 | |
| WO | WO2010/007614 * | 1/2010 | A61N 2/00 |
| WO | 2010135425 A1 | 11/2010 | |
| WO | 2015012672 A1 | 1/2015 | |

OTHER PUBLICATIONS

Polk, "Therapeutic Applications of Low-Frequency Sinusoidal and Pulsed Electric and Magnetic Fields," The Biomedical Engineering Handbook, vol. 1, 2000, Second edition, pp. 1625-1636.
United States Patent and Trademark Office, Non-final Office Action issued in U.S. Appl. No. 15/344,811 (dated Mar. 28, 2017).
United States Patent and Trademark Office, Final Office Action issued in U.S. Appl. No. 15/344,811 (dated Jul. 14, 2017).
United States Patent and Trademark Office, Final Office Action issued in U.S. Appl. No. 14/697,934 (dated May 20, 2016).
United States Patent and Trademark Office, Office Action issued in U.S. Appl. No. 14/697,934 (dated Dec. 17, 2015).
United States Patent and Trademark Office, Final Office Action issued in U.S. Appl. No. 14/700,349 (dated Apr. 18, 2016).
United States Patent and Trademark Office, Office Action issued in U.S. Appl. No. 14/700,349 (dated Nov. 4, 2015).

(56) References Cited

OTHER PUBLICATIONS

United States Patent and Trademark Office, Office Action issued in U.S. Appl. No. 14/789,156 (dated Jun. 29, 2017).
United States Patent and Trademark Office, Final Office Action issued in U.S. Appl. No. 14/789,658 (dated Dec. 1, 2016).
United States Patent and Trademark Office, Office Action issued in U.S. Appl. No. 14/789,658 (dated May 9, 2016).
United States Patent and Trademark Office, Final Office Action issued in U.S. Appl. No. 14/870,713 (dated Jul. 1, 2016).
United States Patent and Trademark Office, Office Action issued in U.S. Appl. No. 14/870,713 (dated Feb. 25, 2016).
United States Patent and Trademark Office, Final Office Action issued in U.S. Appl. No. 14/873,110 (dated Sep. 12, 2016).
United States Patent and Trademark Office, Office Action issued in U.S. Appl. No. 14/873,110 (dated May 4, 2016).
United States Patent and Trademark Office, Office Action issued in U.S. Appl. No. 14/873,110 (dated Feb. 10, 2016).
United States Patent and Trademark Office, Final Office Action issued in U.S. Appl. No. 14/926,365 (dated Aug. 12, 2016).
United States Patent and Trademark Office, Office Action issued in U.S. Appl. No. 14/926,365 (dated Feb. 11, 2016).
United States Patent and Trademark Office, Final Office Action issued in U.S. Appl. No. 14/951,093 (dated Nov. 4, 2016).
United States Patent and Trademark Office, Office Action issued in U.S. Appl. No. 14/951,093 (dated May 9, 2016).
United States Patent and Trademark Office, Final Office Action issued in U.S. Appl. No. 15/073,318 (dated Jan. 4, 2017).
United States Patent and Trademark Office, Office Action issued in U.S. Appl. No. 15/073,318 (dated Jun. 16, 2016).
United States Patent and Trademark Office, Office Action issued in U.S. Appl. No. 15/073,318 (dated Jun. 28, 2017).
United States Patent and Trademark Office, Final Office Action issued in U.S. Appl. No. 15/099,274 (dated Jun. 26, 2017).
United States Patent and Trademark Office, Office Action issued in U.S. Appl. No. 15/099,274 (dated Dec. 12, 2016).
United States Patent and Trademark Office, Final Office Action issued in U.S. Appl. No. 15/151,012 (dated Jun. 22, 2017).
United States Patent and Trademark Office, Office Action issued in U.S. Appl. No. 15/151,012 (dated Dec. 1, 2016).
United States Patent and Trademark Office, Office Action issued in U.S. Appl. No. 15/396,073 (dated Mar. 24, 2017).
United States Patent and Trademark Office, Office Action issued in U.S. Appl. No. 15/471,946 (dated Jun. 30, 2017).
United States Patent and Trademark Office, Office Action issued in U.S. Appl. No. 15/473,390 (dated Jun. 23, 2017).
European Patent Office, PCT/IB2016/053930 International Search Report, dated Dec. 12, 2016.
European Patent Office, PCT/IB2016/053930 Written Opinion, dated Dec. 12, 2016.
Vernon, et al., "Functional Magnetic Stimulation: A New Modality for Enhancing Systemic Fibrinolysis," Arch Phys Med Rehabil vol. 80, May 1999, pp. 545-550.

\* cited by examiner

AESTHETIC METHODS OF BIOLOGICAL STRUCTURE TREATMENT BY MAGNETIC FIELD

PRIORITY CLAIM

This Application is a Continuation-in-Part of U.S. patent application Ser. No. 15/396,073 filed Dec. 30, 2016 and now pending, which is a Continuation-in-Part of U.S. patent application Ser. No. 15/178,455 filed Jun. 9, 2016 and now pending; which is a Continuation-in-Part of U.S. patent application Ser. No. 15/151,012 filed May 10, 2016 and now pending; which is a Continuation-in-Part of U.S. patent application Ser. No. 15/099,274 filed Apr. 14, 2016 and now pending; which is a Continuation-in-Part of U.S. patent application Ser. No. 15/073,318 filed Mar. 17, 2016 and now pending; which is a Continuation-in-Part of U.S. patent application Ser. No. 14/951,093 filed Nov. 24, 2015; which is a Continuation-in-Part of. U.S. patent application Ser. No. 14/926,365 filed Oct. 29, 2015 and now pending; which is a Continuation-in-Part of U.S. patent application Ser. No. 14/789,658 filed Jul. 1, 2015 and now pending; which is a Continuation-in-Part of U.S. patent application Ser. No. 14/789,156 filed Jul. 1, 2015 and now pending. This application is also a Continuation-in-Part of U.S. patent application Ser. No. 15/396,073 filed Nov. 7, 2016 and now pending. The above-listed Applications are incorporated herein by reference.

FIELD OF THE INVENTION

The present invention generally relates to a method using the influence of magnetic and induced electric fields on a biological structure or tissue of a patient. The magnetic field is time-varying and high powered. Therefore the method is based on a value of magnetic flux density sufficient to induce at least partial muscle contraction.

BACKGROUND OF THE INVENTION

Aesthetic medicine comprises all medical procedures that are aimed at improving the visual appearance and satisfaction of the patient. Patients not only want to be in good health, they also want to minimize all imperfections including body shape and effects of natural aging. Indeed, patients request quick, non-invasive procedures providing satisfactory results with minimal risks.

The most common methods used for non-invasive aesthetic medicine applications are based on application of mechanical waves, e.g. ultrasound or shock wave therapy; or electromagnetic waves, e.g. radiofrequency treatment or light treatment, such as intense pulsed light or laser treatment. The effect of mechanical waves on tissue is based especially on cavitation, vibration and/or heat inducing effects. The effect of applications using electromagnetic waves is based especially on heat production in the biological structure.

Skin tissue is composed of three basic elements: epidermis, dermis and hypodermis or so called subcutis. The outer and also the thinnest layer of skin is the epidermis. The dermis consists of collagen, elastic tissue and reticular fibers. The hypodermis is the lowest layer of the skin and contains hair follicle roots, lymphatic vessels, collagen tissue, nerves and also fat forming a subcutaneous white adipose tissue (SWAT). The fat cells create lobules which are bounded by connective tissue, fibrous septa (retinaculum cutis).

Another part of adipose tissue, so called visceral fat, is located in the peritoneal cavity and forms visceral white adipose tissue (VWAT) located between parietal peritoneum and visceral peritoneum, closely below muscle fibers adjoining the hypodermis layer.

Water and biological molecules are diamagnetic substances. The magnetic field is not affected by diamagnetic substances. Therefore no loss of intensity or magnetic flux density occurs when passing through the biological structure or tissue. Therefore the deep biological structures may be treated by the time-varying magnetic field as well. One of the time-varying magnetic fields is the so called pulsed electromagnetic field (PEMF). PEMF is limited by the repetition rate and even by the magnetic flux density. PEMF repetition rates are in range of 5 to 100 Hz and magnetic flux density is up to 600 Gauss (equivalent to 60 mT) based on Physikalische Medizin. [HEISEL, Jürgen. Physikalische Medizin. Stuttgart: Georg Thieme Verlag K G, 2005. ISBN 3-13-139881-7. p. 159]. Another source recites the highest magnetic flux density of 6 mT. [BRONZINO, Joseph, D. The Biomedical Engineering Handbook, Volume I. United States of America: CRC Press LLC, 2000. Second edition. ISBN 0-8493-0461-X. p. 91-1-91-8].

PEMF may be used to improve the conventional non-invasive aesthetic medicine applications, e.g. radiofrequency treatment, diathermy treatment, ultrasound treatment, etc. The enhanced visual results are achieved in combination with these methods as described in US patent application publication US2015025299. The magnetic flux density of the recited magnetic field reaches 20 Gauss and the repetition rate varies from 16 to 25 Hz.

US patent application publication 2015157873 recites an applicator including stimulation coil for emitting magnetic field to the patient to induce muscle contraction for the purpose of fatty tissue breakdown. The magnetic flux density is in range of 0.01 to 0.1 T at distance of 5 cm from the coil surface, the recited repetition rate varies from 10 to 30 Hz and impulse duration is in range of 100 to 300 µs. However, the proposed treatment by magnetic flux density 0.1 T is limited to treat only superficial muscle. Additionally, this treatment may be time consuming and provide limited results. Magnetic flux density of 0.1 T is insufficient to intensively treat superficial muscle or deep biological structures since the magnetic flux density is low. The magnetic flux density is able to treat limited number of muscle fibers. Therefore the muscle contraction is weak and the method is insufficient to be applied for satisfactory enhancement of visual appearance. In order to achieve any results the treatment duration lasts long time period. Accordingly, patients with a high BMI cannot be well treated using existing methods.

Present aesthetic approaches do not provide a method sufficient for visual enhancement by contact and/or contactless use. The above-described methods are limited in key parameters which are repetition rate and/or magnetic flux density. All known methods use low values of magnetic flux density and/or low repetition rates which does not allow satisfactory enhancement of visual appearance. As a result, new methods are needed to enhance the visual appearance of the patient.

SUMMARY OF THE INVENTION

In a first aspect, a method for treatment of a biological structure uses a time-varying magnetic field at a magnetic flux density of at least 0.15 T and/or repetition rate 30 Hz for the purpose of at least a partial muscle contraction and enhancing the visual appearance of the treated body area.

In another aspect, the treatment utilizes non-invasive and/or contactless transfer of the magnetic field from a magnetic field generating device, e.g., a coil. The magnetic field delivered to a biological structure to evoke the action potential of the biological structure to induce at least partial muscle contraction.

The present methods enable new treatments defined by a peak to peak magnetic flux density on the coil surface at least 0.15, 0.2, 0.8, 1.5, 2, 2.4 or up to 7 Tesla at repetition rate at least 1, 10, 30, 50, 55, 60 or up to 700 Hertz with treatment/successive treatments lasting several seconds or longer, for example, for at least 5, 10, 30, 60, 120 or 240 seconds, or longer. The impule duratoin is in the range of tens to hundreds of μs.

In a further aspect, a neuromuscular plate and/or the nerve innervating the neuromuscular plate, is treated and at least partial muscle contraction is provided. The muscle may be contracted at higher repetition rates and the contraction is stronger. Therefore the treatment is more efficient for reducing the number and/or volume of adipose cells and enhancing the visual appearance of the treated body area via targeted muscle contraction. Additionally, strong muscle contractions at higher repetition rates may cause mechanical movement of all the layers in proximity of the contracted muscle. This method therefore causes remodelling and/or neogenesis of the collagen and elastin fibers.

According to another aspect the method may be applied for enhancing the visual appearance of body area including or proximate to major muscle structures. Further the method for enhancing the visual appearance is convenient for treatment of patients with high BMI.

The muscle tissue is selectively treated and the magnetic flux density of the magnetic field may be adjusted based on the patient's feeling and/or needs. Treatment time is shortened due to selective treatment of muscles. Additionally, the treatment may be non-invasive or even contactless due to the high value of magnetic flux density. Invasive methods may be used as well. The patient may be treated without the necessity of taking clothes off. The method reduces patient discomfort.

The present methods may be used for enhancing visual appearance of body areas including adipose tissue reduction, muscle toning, muscle shaping, body contouring, body shaping, skin tightening, cellulite treatment, circumferential reduction, breast enhancement and/or lip enhancement.

GLOSSARY

Conventional non-invasive and/or invasive aesthetic medicine applications refer to aesthetic medicine applications based on application of mechanical waves, e.g. ultrasound or shock wave therapy; or electromagnetic waves, e.g. radiofrequency or diathermy treatment or light treatment, such as intense pulsed light or laser treatment; or mechanical stimulation, e.g. positive or negative pressure, rollerball, massage etc.; or thermal treatment, e.g. cryotherapy; or electrotherapy method; or mesotherapy method and or any combination thereof.

Biological structure/target biological structure includes cells, neurons, nerves, muscle fibers and/or muscle, collagen, elastin, adipose cell tissue.

Treatment refers to a magnetic flux density inducing an electric current in the biological structure.

Body region includes thighs, saddlebags, buttocks, abdomen, hip such as region of love handles, torso such as region of bra fat and/or arm.

Muscle includes at least one of muscle fiber, muscle tissue or group, neuromuscular plate or nerve innervating the at least one muscle fiber.

Deep muscle refers to a muscle that is at least partly below superficial muscles and/or to the muscle that is covered by the thick layer of other tissue, e.g. mostly adipose tissue and/or the skin, with thickness 0.5, 1, 2, 3, 4, 5 or more centimeters.

Impulse refers to a single magnetic stimulus.

Pulse refers to a treatment period including one impulse and time duration of no stimulation, i.e. time duration between two impulses from rise edge to next rise edge.

Repetition rate refers to frequency of firing the pulses; it is derived from the time duration of a pulse.

Figure 1:
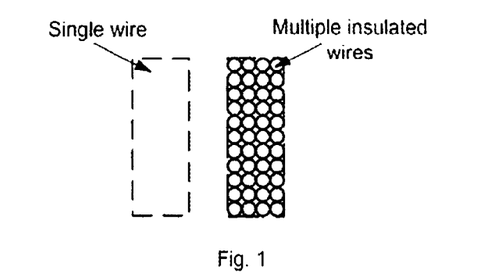
FIG. 1 is a cross section view of a coil winding.

FIG. 1 illustrates a cross section of winding of a coil for a magnetic stimulation device. The coil may be constructed from litz-wire, wherein each wire is insulated separately. Each individual conductor is coated with non-conductive material so the coil constitutes multiple insulated wires. Unlike existing magnetic coil conductors, the present coil is not made of bare wire e.g. litz-wire without insulation, or conductive tapes, conductive strips, or copper pipe with hollow inductors. The insulation of wires separately is a substantial improvement, since this leads to a significant reduction of the induced eddy currents. Power loss due to eddy currents, per single wire, is described by Equation 1 below. The small diameter wires of the present coil significantly reduce self-heating of the coil and therefore increases efficiency of the present magnetic stimulation device:

$$P_{EDDY} = \frac{\pi^2 \cdot B_p^2 \cdot d^2 \cdot f^2}{6 \cdot k \cdot \rho \cdot D}, \qquad \text{Eq. 1}$$

where: $P_{EDDY}$ is power loss per unit mass (W·kg$^{-1}$); $B_p$ is the peak of magnetic field (T); f is frequency (Hz); d is the thickness of the sheet or diameter of the wire (m); k is constant equal to 1 for a thin sheet and 2 for a thin wire; p is the resistivity of material (Ω·m); D is the density of material (kg·m$^3$).

The individual insulation of each wire reduces eddy currents. The individually insulated wires may be wound either one by one or in a bundle of individually insulated wires so as to form a coil, which will serve as a magnetic field generator. The coil provides an improvement in the efficiency of energy transfer in the LC resonant circuit and also reduces or eliminates unwanted thermal effects.

The coil may have a planar coil shape where the individually insulated wires may have cross-section wires with conductor diameter less than 3 mm even more preferably less than 0.5 mm and most preferably less than 0.05 mm.

The wires are preferably made of materials with higher density and higher resistivity e.g. gold, platinum or copper. The diameters of the single wires should be minimal. On the other hand the total diameter should be maximal because of inverse proportion between the cross-section of all wires forming the coil and the electrical resistance. Therefore the ohmic part of the heat is then lower. Eq. 2 describes power loss of the coil:

$$P_R = \frac{\rho \cdot \frac{l}{S} \cdot I^2}{m} \qquad \text{Eq. 2}$$

Where: $P_R$ is the power loss heat dissipation (W); $\rho$ is the resistance ($\Omega \cdot m$); l is the length of wire (m); S is the surface area ($m^2$); I is the current (A) and m is 1 kg of wire material.

Total power loss is (Eq. 3):

$$P_{TOT} = T_{EDDY} + P_R \qquad \text{Eq. 3}$$

Where: $P_{TOT}$ is the total power losses ($W \cdot kg^{-1}$); $P_{EDDY}$ is the power dissipation of eddy currents ($W \cdot kg^{-1}$); $P_R$ is the power loss heat dissipation ($W \cdot kg^{-1}$).

Dynamic forces produced by current pulses passing through the wires of the coil cause vibrations and unwanted noise. The individual insulated wires of the coil may be impregnated under pressure so as to eliminate air bubbles between the individual insulated wires. The space between wires can be filled with suitable material which causes unification, preservation and electric insulation of the system. Suitable rigid impregnation materials like resin, and elastic materials like PTE can be also used. With the coil provided as a solid mass, the vibrations and resonance caused by movements of the individual insulated wires are suppressed. Therefore noise is reduced.

The coil may be attached to the case of the applicator, such as a hand held applicator of the magnetic stimulation device; built-in applicator in e.g. chair, bed; or stand-alone applicator e.g. on mechanical fixture. The attachment may be provided by an elastic material e.g., silicone, gum; or other flexible manner. Connection with the coil of the applicator's case can be ensured by several points. The several fastening points ensure the connection of the coil to the casing by flexible material so that the main part of the coil and the main part of the casing of applicator are spaced apart. The spacing should be at least 0.1 mm so that air can easily flow. The gap between the coil and the casing can be used either for spontaneous or controlled cooling. The coil may optionally be connected to the case of the applicator by only one fastening point. The fastening points eliminate vibrations of wires which could be transferred to housing of the applicator and therefore reduce noise of the magnetic stimulation device.

Figure 2:
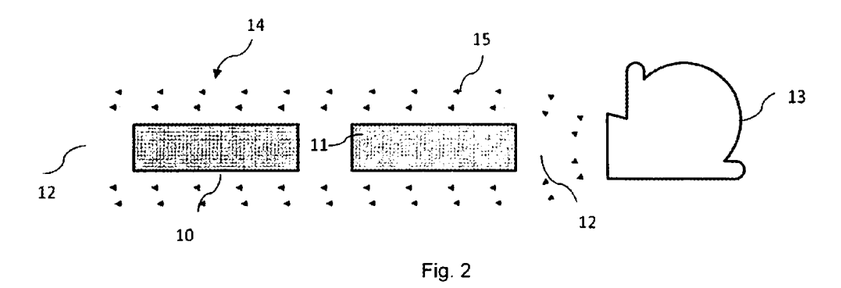
FIG. 2 is an illustrative embodiment of cross-section of the magnetic applicator.

FIG. 2 is a cross-section of the magnetic applicator which allows better flow on the lower and upper sides of the coil and thus more efficient heat dissipation. The magnetic stimulation device includes a coil 10, the circuit wires 11 and the fastening points 12 for connection of the coil to the casing of the applicator (not shown). The fastening points 12 are preferably made of flexible material however the rigid material may be used as well. The fastening points 12 may be located on the outer circumferential side of the coil. However, alternatively it is possible to put these fastening points to a lower or upper side of the coil.

The fastening points 12 connect the coil to the case of the applicator in at least one point. The fastening points 12 maintain the coil and the main part of the case of the applicator spaced apart so that fluid (which may be air or any liquid) can flow between them. At least one blower 13 can be placed around the circumference of the coil, or perpendicular to the coil. The blower can be any known kind of device for directing the fluid e.g. outer air directed into the case of the applicator. This arrangement of the blower allows air to bypass the coil from upper and lower (patient's) sides. In still another embodiment the outer air can be cooled before directing into the case. The blower can have an inlet placed around the circumference of the coil for injecting air, to remove heat from the coil. A connecting tube (not shown) can ensure connection of the applicator 14 with the energy source and/or control unit of magnetic stimulation device. The connecting tube may also contain a conduit of the fluid.

The arrows 15 indicate the air flow through the applicator 14. This arrangement of the blower allows the air to bypass the coil from upper and lower (patient's) side. Outlet may be preferably placed on upper side of the casing. By placing the blower around the circumference of the coil instead of on the top/below the coil, the blower 13 does not interfere with the magnetic flux peak and therefore its lifespan and reliability is increased.

Figure 3:
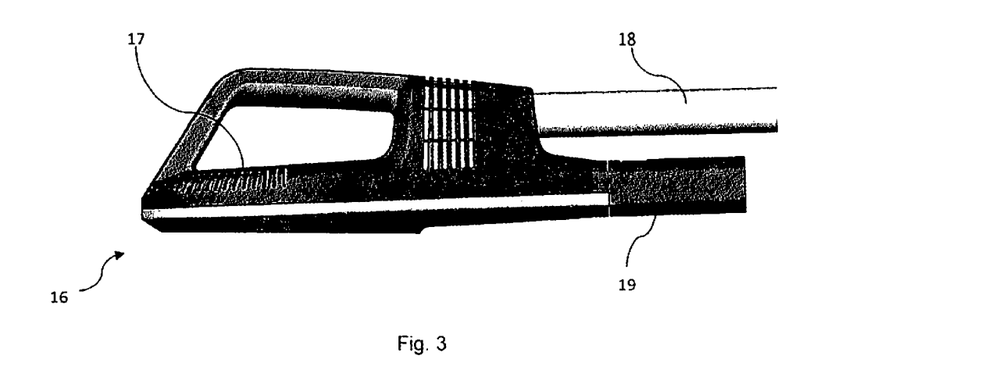
FIG. 3 is an illustrative embodiment of a casing of the magnetic applicator.

FIG. 3 is an illustrative embodiment of a casing of the magnetic applicator. The overview drawing contains casing itself 16, which might contain an outlet 17 preferably placed on upper side of the casing 16. A connecting tube 18 may not only ensure connection of the applicator with the energy source and/or control unit of magnetic stimulation device, but also connection to a source of the fluid; however the conduit of the fluid 19 may also be connected separately.

Figure 4A:
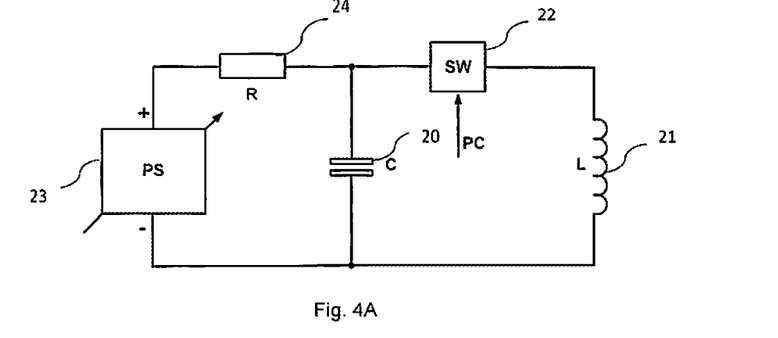
FIGS. 4A and 4B illustrates circuit for providing high power pulses to a stimulating coil.
Figure 4B:
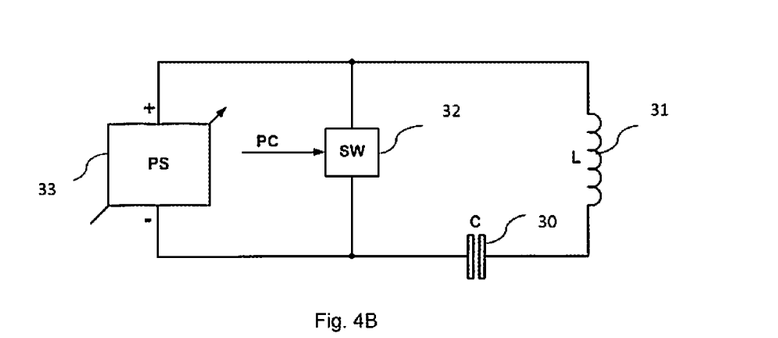

FIG. 4A and FIG. 4B illustrate circuits for providing high power pulses to the stimulating coil. FIG. 4A shows a circuit for providing high power magnetic pulses. FIG. 4B shows a circuit for providing high power pulses.

Existing magnetic stimulation devices achieve magnetic flux density of a few tenths to several Teslas. To achieve this level of magnetic flux density, the energy source used generates sufficient voltage. This voltage can reach thousands of volts. In FIG. 4A the circuits for providing high power pulses to the stimulating coil contain a series connection to the switch 22 and the coil 21. The switch 22 and the coil 21 together are connected in parallel with an energy storage device 20. The energy storage device 20 is charged by the energy source 23 and the energy storage device 20 then discharges through the switching device 22 to the coil 21.

During second half-period of LC resonance, the polarity on the energy storage device 20 is reversed in comparison with the energy source 23. In this second half-period, there is a conflict between energy source 23, where voltage on positive and negative terminals is typically thousands of Volts. The energy storage device 20 is also charged to the positive and negative voltage generally to thousands of Volts. As a result, there is in the circuit, consequently, twice the voltage of the energy source 23. Hence the energy source 23 and all parts connected in the circuit are designed for a high voltage load. Therefore, the protective resistors and/or protection circuitry 24 must be placed between energy source 23 and energy storage device 20. As a result a large amount of energy is transformed to undesired heat in the protective resistors and/or protection circuitry 24.

FIG. 4B shows a circuit for providing high power pulses for improved function of the magnet stimulation device. The coil 31 and an energy storage device 30 are connected in series and disposed in parallel to the switch 32. The energy storage device 30 is charged through the coil 31. To provide an energy pulse, controlled shorting of energy source 33 takes place through the switch 32. In this way the high voltage load at the terminals of the energy source 33 during the second half-period of LC resonance associated with known devices is avoided. The voltage on the terminals of energy source 33 during second half-period of LC resonance is a voltage equal to the voltage drop on the switch 32.

The switch 32 can be any kind of switch such as diode, MOSFET, JFET, IGBT, BJT, thyristor or their combination. Depending on the type of component the load of energy source 33 is reduced to a few Volts, e.g., 1-10 volts. Consequently, it is not necessary to protect the energy source 33 from a high voltage load, e.g., thousands of Volts. The use of protective resistors and/or protection circuits is reduced or eliminated. The present designs simplify the circuits used, increase efficiency of energy usage and provide higher safety.

Figure 5:
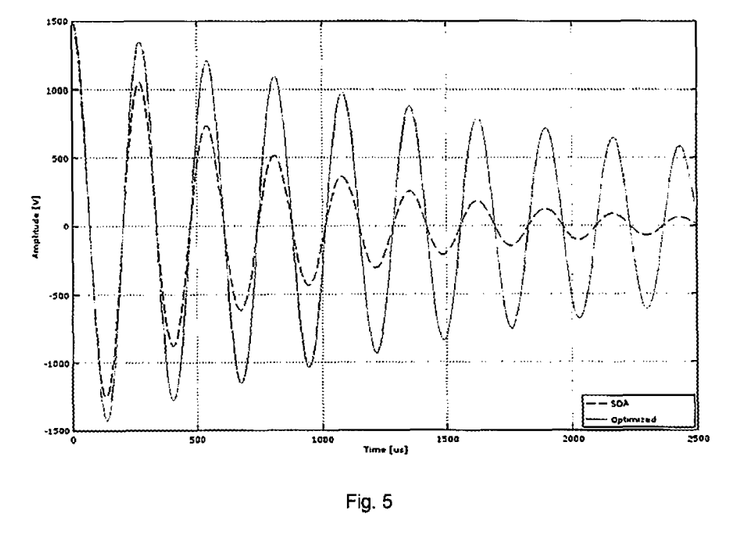
FIG. 5 is a graph showing voltage drop in the energy storage device.

FIG. 5 show an exponential voltage drop in the energy storage device. Energy savings during time-varying magnetic therapy may be characterized by reduced voltage drop in the energy storage device between the first, second and subsequent maximums of the resonant oscillation. The magnitude of the individual voltage oscillations is exponentially dampened up to establishing the energy balance. This allows increasing the maximum possible frequency/repetition rate of magnetic pulses, since the frequency/repetition rate is dependent on the speed with which it is possible to recharge the energy storage device. Since the energy storage device is recharged by the amount of energy loss during the previous pulse, it is possible to increase the frequency/repetition rate of the device up to hundreds of magnetic pulses per second without the need to increase the input power. The voltage drop between any of the successive amplitudes is not higher than 21%, even more preferably not higher than 14% and most preferably not higher than 7%.

The device can be used for treatment/successive treatments in continual, interrupted or various duty cycle regime. The duty cycle may be higher than 10%, which means interrupted regime with the ratio up to 1 active to 9 passive time units. The ratio may possibly change during the therapy. The device enables operation defined by the peak to peak magnetic flux density on the coil surface at least 3 T, more preferably at least 2.25 T, most preferably at least 1.5 T at repetition rates above 50 Hz, more preferably at repetition rates above 60 Hz, even more preferably at repetition rates above 70, most preferably at repetition rates above 80 Hz with treatment/successive treatments lasting several seconds or longer, for example, for at least 5, 10, 30, 60, 120 or 240 seconds, or longer. The total power consumption is below 1.3 kW and the width of pulses is in the range of hundreds of µs.

The device enables achieving repetition rates above 100 Hz, more preferably repetition rates above 150 Hz, most preferably repetition rates above 200 Hz with the magnetic flux density providing a therapeutic effect on neurons and/or muscle fibers and/or endocrine cells (e.g. at least partial muscle contraction, action potential in cell). Based on achievement of repetition rates in order of few hundreds the device also enables assembling the magnetic pulses into the various shapes (e.g. triangular, rectangular, exponential), with the shape widths from 6 ms to several seconds or longer.

DETAILED DESCRIPTION

Electric current is induced in the biological structure treated by time-varying magnetic field. Due to the high value of magnetic flux density the biological structure may be targeted and treated more specifically. A distribution of magnetic field may be uniform in the biological structure. Particles (e.g. atoms, ions, molecules etc.) in the biological structures may be influenced by the magnetic field and permeability of a cell membrane also increases.

Due to increased permeability of the cell membrane, the pulsed magnetic treatment may induce following effects: at least partial muscle contraction; reduction of adipose tissue—volume and/or number of the adipose cells; neogenesis and/or remodelling of collagen and/or elastin fibers; improving circulation of blood and/or lymph and improves local and/or adipose tissue metabolism.

With the present methods, factors for enhancing visual appearance of the body may be: treatment of major muscle, e.g. gluteus maximus; treatment of deep muscle which may be enabled by high value of magnetic flux density; non-contact application of magnetic flux density, it may be applied even through clothing; stronger muscle contraction due to higher value of magnetic flux density; higher-quality of muscle targeting; treatment is not influenced by small movements during treatment; treatment time duration may be shortened due to high value of magnetic flux density and/or higher repetition rate; no delays occur.

It is to be understood that the method is not limited to the particular applications and the method may be practiced or carried out in various ways.

The present method may be applied for enhancing the visual appearance of body parts including or proximate to major muscle structures. Further the method may be applicable for enhancing the visual appearance of patients with high value of BMI. The patient may be preferably healthy without any life-threatening conditions such as circulatory system diseases, e.g. a deep vein thrombosis. The present method is not limited to the application of the treatment to major muscle. Muscles other than major muscles may be treated as well.

In the preferred application the treatment method may be applied to body regions prone to cellulite and/or prone to adipose accumulation, e.g., thighs, saddlebags, buttocks, abdomen, hips such as in a region of love handles, torso such as in a region of bra fat or arm. The adipose accumulation may be influenced by number and/or volume of adipose cells.

The present method may include the step of screening the patient to exclude patients having certain conditions, such as described above, and then treating only healthy patients with the present method, and then treating such screen patients only for one of the conditions described herein. In some applications the present method may provide only one or more of the therapeutic benefits described herein, without providing any other therapeutic or medical treatment.

The magnetic field generating device may be placed proximate to the patient's body. As used here, proximate to includes both contactless and in actual contact with the skin of the patient. The muscles may be selectively treated by magnetic field of the magnetic flux density which may be adjusted following the patient's feeling or needs. The treatment time may be shortened due to selective treatment of the correct muscles. Additionally, due to the high value of magnetic flux density, the muscle may be treated more effectively. Further, the treatment may be non-invasive or even preferably contactless due to the high value of magnetic flux density. The patient may be treated without removing clothing, reducing patient discomfort. The position of the patient may correspond to treated biological structure and/or body region. The patient may be treated in seated position. Alternatively, the patient may be treated in lying position, preferably in a supine position, or the patient may be treated in a lateral recumbent position. Alternatively, the patient may be in a prone position as well. Additionally, following the high efficiency of the muscle contraction the collagen and/or elastin fibers above the muscle structure may be remodelled, hence the visual appearance may be enhanced.

The magnetic treatment of the biological structure has various applications for enhancing visual appearance of the contour body area. High density magnetic field reaches such values which may be used for: adipose tissue reduction, wherein the adipose tissue reduction may be achieved by reduction of number and/or volume of adipose cells; muscle toning, wherein the muscle appearance enhancement may be achieved by adipose tissue reduction with no muscle bulking; muscle shaping, wherein the muscle appearance enhancement may be achieved by adipose tissue reduction and/or muscle bulking; body contouring, wherein the silhouette appearance enhancement may be achieved by adipose tissue reduction with no muscle bulking; body shaping, wherein the silhouette appearance enhancement may be achieved by adipose tissue reduction and/or muscle bulking; skin tightening, wherein the skin appearance enhancement may be achieved by obtaining smoother and younger appearance, including wrinkles reduction; cellulite treatment, wherein the appearance enhancement may be achieved by adipose tissue reduction, muscle contraction and/or elastic fibers neogenesis; circumferential reduction, wherein the reduction may be achieved by adipose tissue reduction and/or the muscle bulking; breast enhancement, wherein the appearance enhancement effect may be achieved by elevation or shape modification; lip enhancement, wherein the lip appearance enhancement may be achieved by obtaining fuller and firmer appearance. The body area treated may be reduced in overall size.

In the methods described, the magnetic stimulation device may or may not include a magnetic core. The magnetic stimulation device may be cooled by fluid, e.g. by air. Total power consumption of the magnetic stimulation device may be below 1.3 kW. A magnetic stimulation device as described in the U.S. patent application Ser. No. 14,789,156 or U.S. patent application Ser. No. 14,789,658, incorporated herein by reference, may be used.

The magnetic field generating device may be placed proximate to the patient's body. The magnetic flux density is applied into the target biological structure. Electric current may be induced and may treat the neuromuscular plate and/or the nerve innervating the at least one muscle fiber. The treatment may cause at least a partial muscle contraction.

The present method may treat the biological structure by time-varying magnetic field. The peak to peak magnetic flux density on the coil surface may be at least 0.15, 0.2, 0.8, 1.5, 2, 2.4 or up to 7 Tesla at repetition rate at least 1, 10, 30, 50, 55, 60, or up to 700 Hertz with treatment/successive treatments lasting several seconds or longer, for example, for at least 5, 10, 30, 60, 120 or 240 seconds, or longer. The impulse duration may be in the range of tens to hundreds of ps. The magnetic stimulation device may emit no radiation.

The magnetic field may treat at least one muscle for improving its functionality and/or the appearance with results similar to body exercise. The results may be achieved by application of high magnetic flux density to the body area and inducing at least partial muscle contraction. Higher values of magnetic flux density applied may result in a stronger muscle contraction. The patient may feel firmer and tighter.

With the present method muscle contractions induced by the applied magnetic flux density may help to tone the muscle providing a more attractive appearance. As the muscle structure is treated by time-varying magnetic field the entire limb may be moved due to the high power of the magnetic treatment. Nevertheless, the method is not limited to the applications to the limbs and the method is able to treat any muscle, e.g. gluteus maximus or any muscle/deep muscle to induce body contouring and/or body shaping effect and fat burn. Additionally, shortened and/or flabby muscles may be stretched. The physical fitness of the patient may be improved as well.

The magnetic field may treat various parts of the patient's body, e.g. thighs, buttocks, hips, abdomen or arms. The muscles may be shaped to enhance visual appearance of the treated area. The body part may obtain enhanced visual appearance of its contour.

The magnetic field may treat at least one muscle of lower limb, particularly the part which is prone to cellulite such as thighs or saddlebags. The time-varying magnetic field may induce at least partial muscle contraction in different muscle groups. Following the position and/or orientation of the magnetic field generating device the anterior, posterior and/or medial compartment of the thigh may be treated. The anterior compartment includes sartorius muscle, rectus femoris muscle, vastus lateralis muscle, vastus intermedius muscle, vastus medialis muscle. Posterior compartment includes biceps femoris muscle, semitendinosus muscle and semimembranosus muscle. Medial compartment includes pectineus muscle, external obturator muscle, gracilis muscle, adductor longus muscle, adductor brevis muscle and adductor magnus muscle.

The treatment may cause circumferential reduction of thighs. Further the muscle may obtain enhanced visual appearance, thigh may be well-shaped. Thigh contour may be enhanced as well.

The at least one surrounding body region may be treated as well, e.g. a buttocks.

The magnetic field may treat at least one muscle of buttocks, e.g. at least one muscle providing a shape to the buttocks may be treated, e.g. tensor fasciae latae muscle or at least one of gluteal muscles: maximus, medius or minimus. In one preferred application all three gluteal muscles may be treated. Further muscles in surroundings may be also treated, e.g. abdominal muscles, spinal muscles and/or thoracic muscles. By the complex treatment and muscle contraction in the target area the treated muscles may be strengthened and/or toned. The cellulite may be reduced and dimples may be removed. Buttocks and even the patient's figure may obtain enhanced visual appearance and become more attractive. Buttocks may become well-shaped, round, firm, well-trained, toned, smoother, tighter and/or lifted. The complex treatment may reduce hips, make perfect round and lifted buttocks and increase the self-confidence of the patient The treatment by time-varying magnetic field may induce the same effect as muscle exercising. The treatment is more efficient than standard workout in fitness since the fitness machines strengthen only the isolated muscles. The results may be achieved in very short-time periods with minimal time of the treatment. Without being limited, it is believed that the exercising of the gluteus medius may reduce the volume of the buttocks; exercising of the gluteus maximus may shape and/or lift the buttocks; exercising of the gluteus minimus may lift the buttocks.

The magnetic treatment may also treat at least one surrounding body region, e.g. thighs and/or saddlebags.

The magnetic field may treat at least one muscle responsible for the shape or silhouette of the body. The time-varying magnetic field may induce at least partial muscle contraction in different muscle and/or muscle groups responsible for silhouette in the region of abdomen, love handles and/or bra fat. Following the position and/or orientation of the magnetic field generating device rectus abdominis muscle may be treated. Alternatively latissimus dorsi muscle, abdominal internal oblique muscle, abdominal external oblique muscle, transverse abdominal muscle and/or pyramidalis muscle may be treated by the time-varying magnetic field.

The treatment may cause circumferential reduction in the area of belly, hips and/or love handles. Alternatively the treatment may tighten at least one of these body parts. Further the muscles may obtain enhanced visual appearance, belly may be well-shaped. Repetitive application may even reach in a six-pack look. The surrounding body region may be treated as well, e.g. a buttocks.

The magnetic field may treat muscles of upper limb, particularly the part which are prone to cellulite such as arms. The time-varying magnetic field may induce at least partial muscle contraction. Following the position and/or orientation of the magnetic field generating device the at least partial muscle contraction may occur in biceps brachii muscle, brachialis muscle, coracobrachialis muscle and/or triceps brachii muscle.

The treatment may cause circumferential reduction of the arm. Further the muscle may obtain enhanced visual appearance, arm may be well-shaped. Arm contour may be enhanced as well.

The present methods may also induce muscle contraction to reduce effect of skin laxity. Skin laxity may be caused by e.g. the aging process or increasing number and/or volume of adipose cells which pulls down the skin by gravity, rapid weight loss or skin stretching during the pregnancy. The muscles may be treated by the induced electric current to contract. Repetitive contractions may cause the muscles to obtain the tonus and flexibility. Therefore the skin appearance may be enhanced by treating the flabby muscles. The effect of skin tightening may be achieved. The method also may promote the creation of the collagen and elastin fibers in the layers subtending the epidermis hence the skin may obtain enhanced visual appearance. The method may be widely applied but not limited to application to the regions of neck, breasts, arms or abdomen. The method may provide the smoother and younger appearance of the skin to the patient.

Similar methods of treating the muscle structure by time-varying magnetic field for inducing the at least partial muscle contraction may be used for treatment of wrinkles as well. Wrinkles may be results of extrinsic and intrinsic factors. Nowadays, wrinkles are considered to be negative effect of natural aging process which decreases the production of collagen and elastin fibers and weakens the skin which becomes thinner. As the treatment by the magnetic flux density may induce at least partial muscle contraction, the stimulation of collagen and elastin fibers neogenesis may be improved. Additionally, the muscles subtending the treated region may be toned and the skin may get a younger and enhanced visual appearance. Therefore, the effect of skin tightening may be achieved.

Wrinkles may be prevented or reduced by practising facial exercises which may cause a massage effect to the facial tissues, improving blood and lymph circulation. Additionally, the facial muscles may be relaxed and toned after the exercise. A similar effect as facial exercise may be achieved by non-invasive and/or contactless method of treating the facial muscles by magnetic flux density. Further additional advantage of the present method may be improvement of restoration of the collagen and/or elastin fibers, more effective toning and strengthening of the facial muscles.

The present methods may improve the neogenesis and/or remodelling of collagen fibers in the lips to reach a full, plump and firmer appearance. The magnetic flux density may be applied to the lips by an applicator. Therefore the lips may become fuller and firmer without any need of invasive method such as injection of the synthetic fillers, permanent makeup or the facial implants. The present method may influence the remodelling and/or neogenesis of collagen fibers in a natural way. Additionally, the collagen is natural substance of the human body which provides the elasticity to the structure.

The present methods may be used for enhancing the visual appearance of breasts. Cooper's ligament may be treated, improved and/or firmed by the at least partial muscle contraction. The muscle treatment may induce the elevation of the breast tissue. Additionally, the breast tissue may be treated to be modified in a shape, wherein the shape includes the size and/or the contour of the breast tissue. Therefore the visual appearance may be enhanced and breasts may obtain more attractive appearance for the patient. The present method is a non-invasive alternative for current aesthetic surgery method for the treatment of sagging breast tissue. The present method may provide a patient a method of breast visual appearance enhancement without surgery. Therefore the method lacks post-surgery complications such as scars, postoperative pain or long recovery period.

The present method may provide a massage effect via the treatment which may be caused by the at least partial muscle contraction. Therefore the massage effect may be achieved by contactless methods instead of manual massage techniques or soft tissue techniques. The massage effect may improve lymph circulation.

Cellulite is an effect of skin change resulting in orange peel appearance. The cause of the cellulite may be orientation of collagen fibers in so called "fibrous" septae. The fibrous septae contract and harden over time creating a dimple effect. Additionally, blood and lymphatic vessels may lack circulation due to the contraction and hardening of the septae. The lymph flow may be blocked resulting in swelling. Another cause of cellulite may be adipose cells protruding to dermis. Cellulite may be treated by the recited methods.

One application of time-varying magnetic field for enhancing the visual appearance of body region may be treating of a muscle by magnetic flux density for reducing the cellulite. The magnetic field may be delivered through the skin to the neuromuscular plate and/or nerve innervating at least one muscle fiber. The electric current may be induced in the target biological structure causing at least partial muscle contraction. The at least partial muscle contraction may cause the movement of the skin and all the biological structures subtending epidermis. Additionally, the at least partial muscle contraction may improve blood circulation by itself, or via the movement of the muscle in the vicinity including fibrous septae. Additionally, blood and/or lymph circulation may be improved in the layers subtending epidermis since the muscle contraction may move the fibrous septae. Also local and/or adipose tissue metabolism may be improved.

Treatment by time-varying magnetic field may induce lipolysis. Adipose tissue may be reduced by decreasing the number and/or volume of adipose cells. Promoted adipose cell metabolism may increase as the value of magnetic flux density increases. The treatment may release free fatty acids (FFA) from at least one adipose cell. The increased concentration of FFA may influence a homeostasis of the adipose cell. A disruption of the homeostasis may cause a dysfunction of the adipose cell. The dysfunction may be followed by stress for endoplasmic reticulum (ER stress). ER stress may cause additional lipolysis and/or apoptosis of the at least one adipose cell.

Furthermore, ER stress may cause increase of intracellular calcium ions (Ca2+) which may promote an apoptotic process and may continue into controlled cell death of the adipose cell. The apoptosis may be induced by Ca-dependent effectors, e.g. calpain or caspase-12. Endogenous ligands or pharmacological agents, such as vitamin D, may induce prolonged cytosolic calcium increase. Vitamin D may influence release of Ca2+ from endoplasmic reticulum. Hence the effect of treatment may be enhanced by application of vitamin D and/or Ca2+ prior, during and/or after the treatment. The most significant effect may be achieved by application of both, Ca2+ and vitamin D, prior the treatment to provide all factors influencing adipose cell apoptosis.

Alternatively, increased level of Ca2+ may induce autophagy within adipose cell as well. Autophagy is self-eating process of cellular organelles to produce energy and it may proceed into cell death. Autophagy may be induced by ER stress or it may be induced via Ca2+ signaling.

Figure 6:
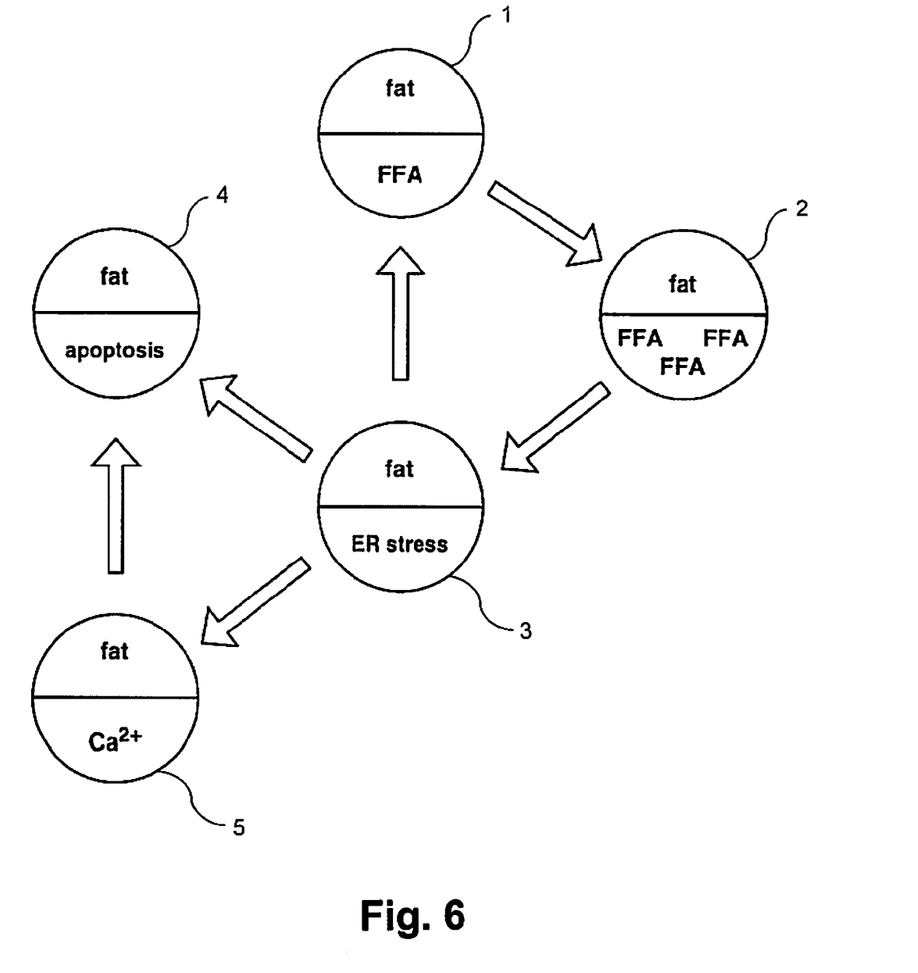
FIG. 6 illustrates a scheme of reduction of the number and/or volume of adipose cells.

FIG. 6 illustrates pathways which may induce apoptosis of the at least one adipose cell. The magnetic field may induce lipolysis, i.e. a release of FFA from adipose tissue (1). FFA may accumulate in the at least one adipose cell (2). Accumulated FFA may reach a threshold when adipose cell is unable to utilize FFA. A dysfunction of the adipose cell may occur. The adipose cell may react on the dysfunction by ER stress (3). ER stress may induce lipolysis hence additional release of FFA may occur (1). ER stress may cause apoptosis of the adipose cell (4). Furthermore, the ER stress may release Ca2+ (5) which may contribute the apoptosis (4).

The effect of the treatment by magnetic field for adipose tissue reduction may be influenced by various biological processes and/or pathways as recited above. The processes and/or pathways may be synergic hence the adipose tissue reduction may be accelerated and/or more efficient.

The method may cause the circumferential reduction i.e. a reduction of the size of the treated body area. The method may be mostly indicated for the regions with cellulite, especially for thighs, buttocks, saddlebags, love handles, abdomen, hips and/or arms. However, the indication is not limited to the mentioned regions and the method may be used for treatment of any other body area.

Various treatment protocols may be used.

Following the recited methods the treatment may be but is not limited to continuous, pulsed, randomized or burst. The impulse may be but not limited to monophasic, polyphasic and/or biphasic.

In the preferred application of the present method the trains of pulses, called bursts may be used.

Repetition rate, magnetic flux density and/or impulse duration may vary during the treatment protocol. Further the magnetic treatment may include several periods of pulses of different repetition rates, therefore the treatment may be modulated in repetition rate domain. The treatment may include several periods of impulses of different magnetic flux densities, therefore the treatment may be modulated in magnetic flux density domain. The treatment may include impulse of different impulse duration, therefore the treatment may be modulated in impulse duratiuon domain. In yet another approach the envelope of the magnetic treatment may be modulated by any combination thereof.

Various envelopes of the magnetic field and waveform, e.g. pulse, sinusoidal, rectangular, square, triangular, sawtooth, trapezoidal, exponential etc. for the purpose of muscle treatment may also be used, and are not limited to recited shapes.

The values of magnetic flux density and repetition rate are cited in several preferred applications since the perception of the treatment may be subjective. Nevertheless, the magnetic flux density and repetition rates are not limited by the recited values. A person skilled in the physical therapy is able to repeat and apply the treatment methods adjusting the magnetic flux density and/or repetition rate following the patient's sensitivity or needs.

All the recited methods may be applied to a patient in a non-invasive and/or contactless way. Therefore the present methods may provide an effective alternative approach of enhancing the visual appearance with no need of invasive treatment or surgery. Further, the visual results may be appreciable after several treatments. Additionally, the results may include not only the visual appearance enhancement but even the improvement of the muscle structure. Hence the patient may feel firmer and tighter. The muscle structures may become toned with no need of any diet or spending time by exercising in fitness.

The patient may feel firmer and/or tighter. The skin may be also tighter. Additionally, adipose tissue reduction may occur. Furthermore, cellulite may be reduced as well.

For enhancing the result the method may be combined with other treatment methods using different approaches, e.g. conventional non-invasive treatments. The combined treatment may be applied to provide synergic effect and to promote the enhanced visual appearace in shorter time.

Thus, novel systems and methods have been described. Various changes and substitutions may of course be made without departing from the spirit and scope of the invention. The invention, therefore, should not be limited, except by the following claims and their equivalents.

The invention claimed is:

1. A method for toning and/or strengthening a muscle of a patient using a treatment device including a connection to energy source, a switching device enabling repetitively generating a magnetic field, and an energy storage device connected to a magnetic field generating device, comprising:
   a. charging the energy storage device to provide energy to the magnetic field generating device;
   b. applying a single pulse of a time-varying magnetic field to the muscle of the patient;
   wherein the time-varying magnetic field causes a contraction of the muscle; and
   wherein energy loss between any of successive amplitudes of the time-varying magnetic field is not higher than 21%.

2. The method of claim 1 wherein an impulse duration of the time-varying magnetic field is up to 900 μs.

3. The method of claim 2 wherein a magnetic flux density of the time-varying magnetic field is at least 0.2 T; and
   wherein a repetition rate of the impulses of the time-varying magnetic field is up to 100 Hz.

4. The method of claim 1 wherein the method further comprises repetitively switching the switching device on.

5. The method of claim 1 wherein the switching device is in a parallel connection to the energy source.

6. The method of claim 1 wherein the treatment device has a power consumption below 1.3 kW.

7. A method for reducing cellulite of a patient using a device including a connection to an energy source, a switching device, an energy storage device and a magnetic field generating device comprising:
   a. providing energy from the energy storage device to the magnetic field generating device in order to generate a time-varying magnetic field;
   b. applying the time-varying magnetic field to the patient;
   c. cooling the magnetic field generating device;
   d. repetitively switching the switching device on in order to generate the magnetic field;
   wherein an impulse duration of the time-varying magnetic field is up to 900 μs; and
   wherein an energy loss between any successive amplitudes of the time-varying magnetic field is not higher than 21%.

8. The method of claim 7 wherein the magnetic field generating device is within a casing; and
   wherein the casing is in actual contact with the patient.

9. The method of claim 7 wherein the energy storage device is in serial connection with the magnetic field generating device.

10. The method of claim 7 wherein the method further comprises controlled shorting of the energy source.

11. The method of claim 7 wherein the method further comprises generating the magnetic field with a magnetic flux density of at least 0.15 T; and
   applying the time-varying magnetic field with a repetition rate of at least 1 Hz.

* * * * *